(12) United States Patent
Chung

(10) Patent No.: US 6,188,072 B1
(45) Date of Patent: Feb. 13, 2001

(54) APPARATUS FOR EXTRACTING TEM SPECIMENS OF SEMICONDUCTOR DEVICES

(75) Inventor: Chao-Shi Chung, Chu-Pei (TW)

(73) Assignee: Mosel Vitelic Inc., Hsin-Chu (TW)

( * ) Notice: Under 35 U.S.C. 154(b), the term of this patent shall be extended for 0 days.

(21) Appl. No.: 09/327,491

(22) Filed: Jun. 8, 1999

(51) Int. Cl.[7] .................................................. H01J 37/20
(52) U.S. Cl. ........................................................ 250/442.11
(58) Field of Search ............................. 250/442.11, 311

(56) References Cited

U.S. PATENT DOCUMENTS 3,835,338 * 9/1974 Martin .............................. 250/442.11

* cited by examiner

Primary Examiner—Kiet T. Nguyen
(74) Attorney, Agent, or Firm—Bacon & Thomas

(57) ABSTRACT

An apparatus for extracting TEM specimens of semiconductor devices is disclosed. The apparatus includes an extracting assemblage which comprises a pipette; and shifting assemblages, which connect to the extracting assemblage, used to control the movement of the pipette.

19 Claims, 7 Drawing Sheets

APPARATUS FOR EXTRACTING TEM SPECIMENS OF SEMICONDUCTOR DEVICES

BACKGROUND OF THE INVENTION

1. Field of the Invention

The present invention relates to micro-analytic technologies, more particularly to an apparatus for extracting TEM specimens of semiconductor devices.

2. Description of the Prior Art

Micro-analytic technologies have been used in a wide range of applications in IC industry. The tolerance for defect size in IC wafer is limited more than ever, and the ability of micro-analytic apparatus should be enhanced. In general, micro-analytic apparatus is used for aspect analysis and composition analysis. For aspect analysis, transmission electron microscope (TEM) can provide information about phase contrast, atomic lattice imaging and others. The TEM specimens are easy to prepare, and developed day after day.

The new technology for preparing TEM specimen is disclosed by FEI company, and described below summarily:

(1). The wafer or die based navigation software in the FIB is used to locate a specific defect site. The other processes involve dicing the wafer, mechanically polishing the sliced specimen.

(2). The focused ion beam (FIB) is used for final thinning to form the specimen which is 10 μm long, 0.2 μm thick, and 8 μm deep.

(3). Under both a TEM specimen extractor and an optical microscope (OM), a specimen is extracted and removed from the wafer by electrostatic attraction existing on the tip of a pipette fixed on the TEM specimen extractor. Finally, the specimen is dropped on the grid, and then TEM is subsequently used to analyze the specimen.

A probe station primarily used as an electroscope is converted into the TEM specimen extractor which is described above and has a very high price. In the TEM specimen extractor, 5 rotary buttons, of which 3 are for coarse adjustments in X, Y, Z directions and 2 are for fine adjustments in X, Y directions, are used to control movement of the pipette. Therein, to move the pipette in the same direction, a coarse and a fine rotary button should be turned respectively in the opposite direction. The complicated manipulation usually causes failure in extracting. In fact, the pipette, of which diameter of tip side is about 2 μm, usually breaks when it touches the wafer. That's due to wrong direction or too many adjustments. In addition, the wafer is also damaged. For the reason described previously, an operator should be given a long-time training. Moreover, the driving device of the extractor, the assemblage of gears and chains, will give the extractor lower accuracy about locating ability after used for a few times. Therefore, practicability of the extractor will be also reduced.

For the foregoing reasons, there is a need to develop an extracting apparatus which provides a lower price, easier manipulation, and high success rate of extracting.

SUMMARY OF THE INVENTION

In accordance with the present invention, an apparatus is provided for extracting TEM specimens of semiconductor devices. It has properties of simple structure, lower cost, easier manipulation, high success rate of extracting. The requirements for manufacture of semiconductor devices could be satisfied.

In one embodiment of the present invention, an apparatus mainly comprises: a base, X, Y, and Z-direction shifting assemblages, a L-shape support, and an extracting assemblage. A glass pipette, fastened in the extracting assemblage, with the electro-static attraction is used to attract the very small TEM specimen. A contractible fastener, used to fasten the glass pipette. The X, Y, and Z-direction shifting assemblages are used to control movement of the glass pipette. Therein, to provide a continuous movement for the glass pipette, ball-track devices and springs are used. In addition, to control the moving distances in X, Y, and Z directions, micrometers are used. For the apparatus, it's easy to manipulate and to extract the TEM specimen accurately. Therefore, the success rate of extracting is increased. Both the time and the cost of manufacture are reduced by the way.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
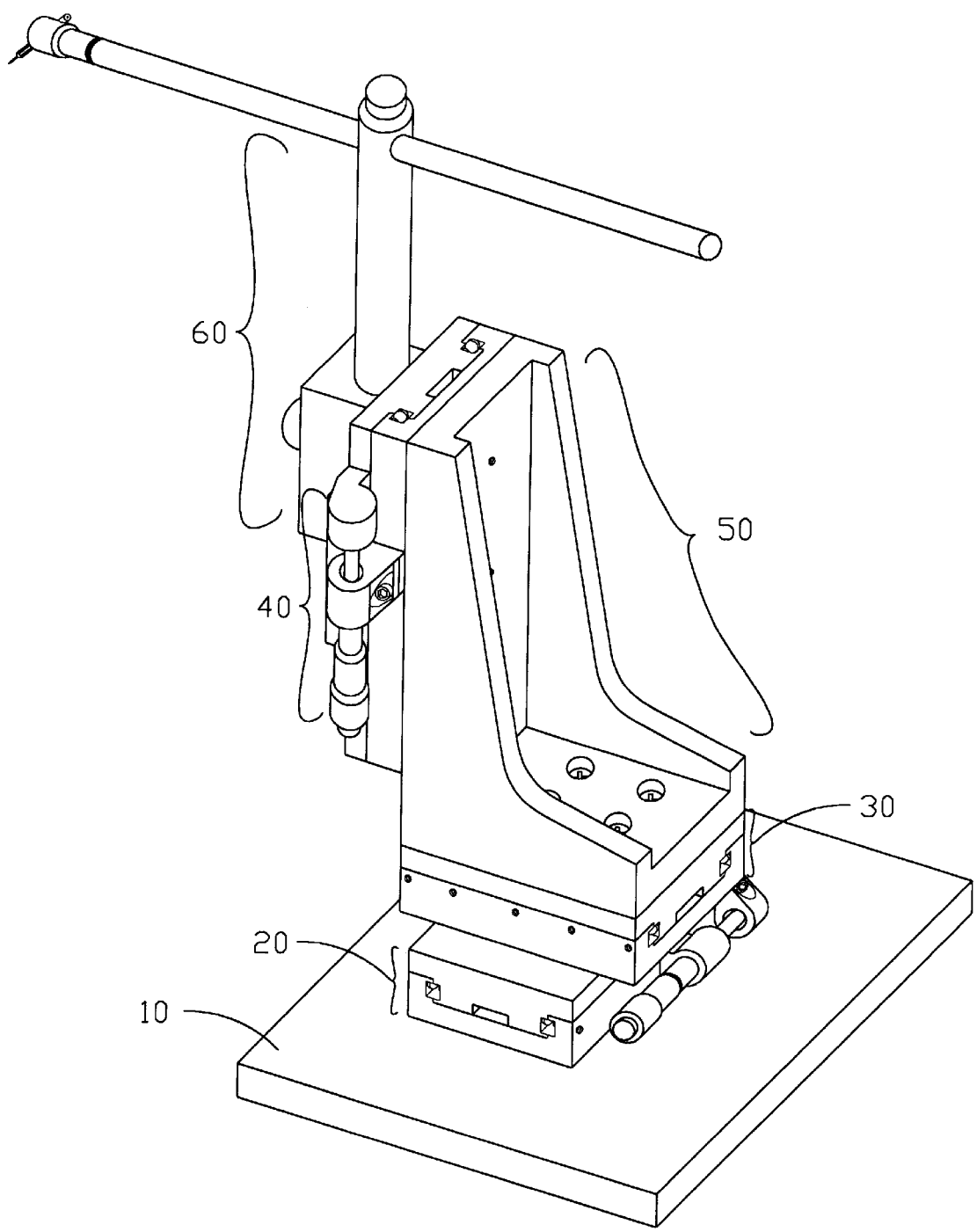
FIG. 1 shows the whole view of the present invention named 3-direction TEM specimen extractor.

The whole view of the present invention is shown as FIG. 1.

Figure 2:
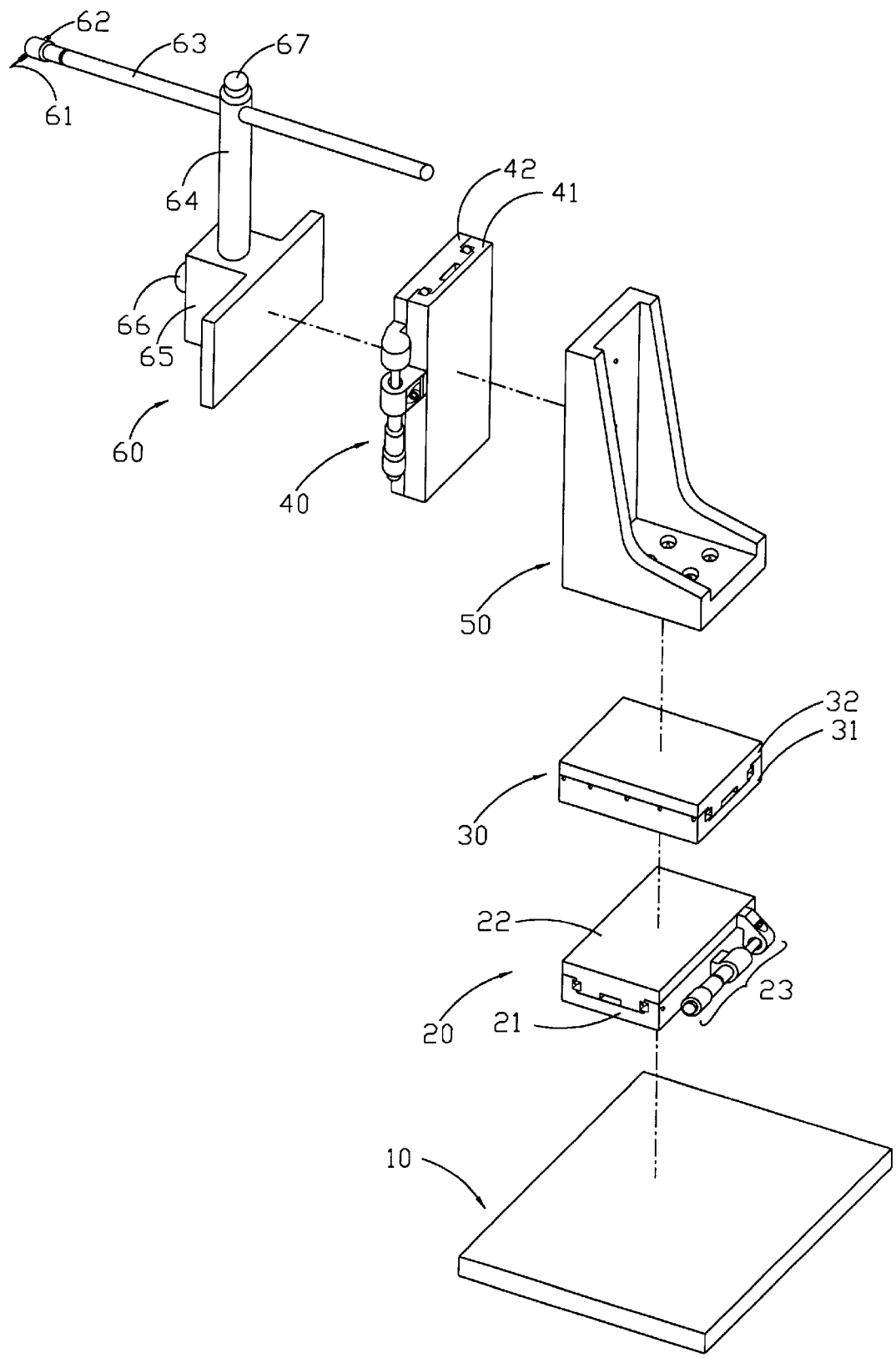
FIG. 2 shows the cut-off views of the present invention.

Referring to FIG. 2, the apparatus includes a base 10, X, Y, and Z-direction shifting assemblages 20, 30, 40, a L-shape support 50, an extracting assemblage 60. Therein, the X, Y, and Z-direction shifting assemblages, used to control movement of extracting device, can lead the extracting device to the specimen on the wafer exactly. The base 10, such as a square metal, is located at the bottom of the apparatus and used to keep the apparatus steady.

Figure 3:
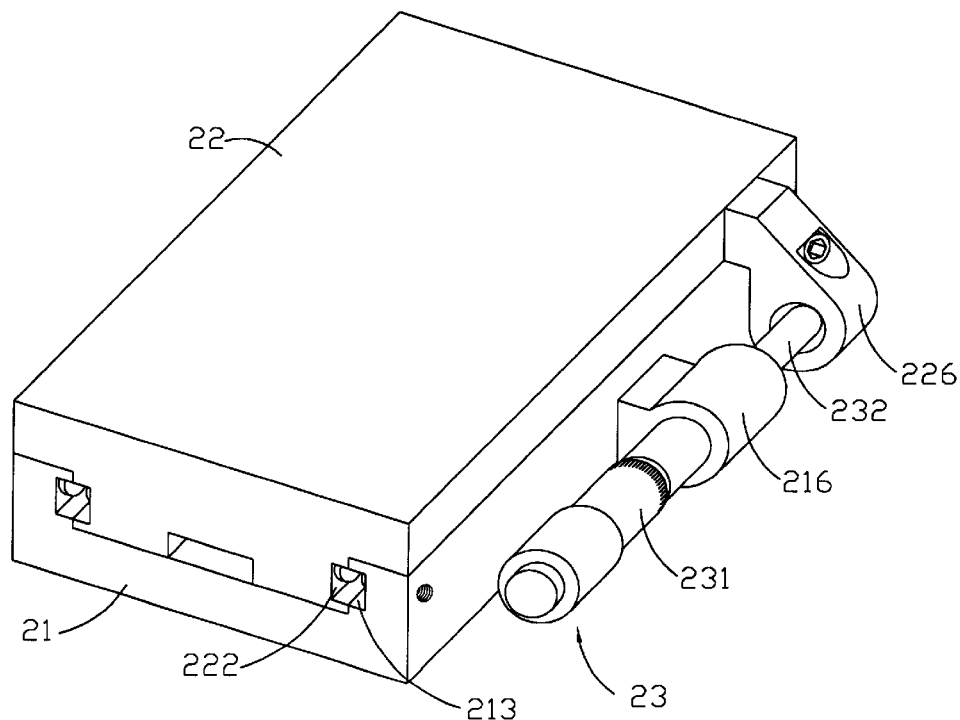
FIG. 3 shows the X-direction shifting assemblage.
Figure 3A:
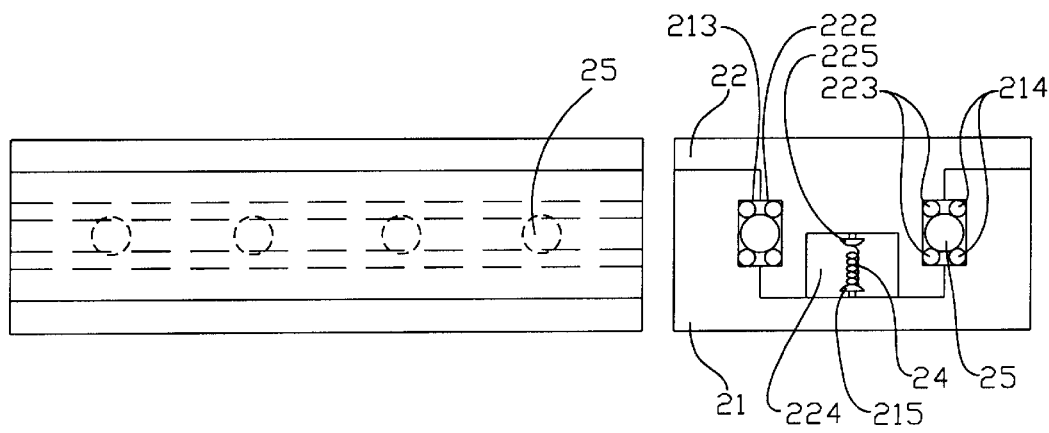
FIG. 3A shows mainly the side view of the shifting assemblage containing the balls that are arranged.
Figure 3B:
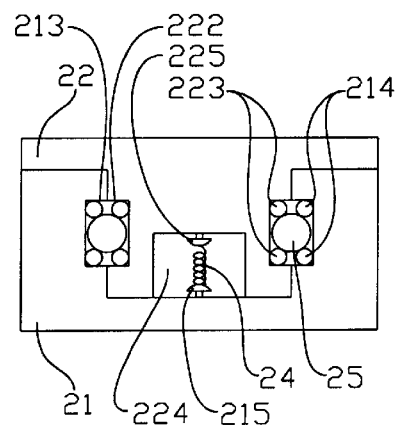
FIG. 3B shows the front view of the shifting assemblage.
Figure 3C:
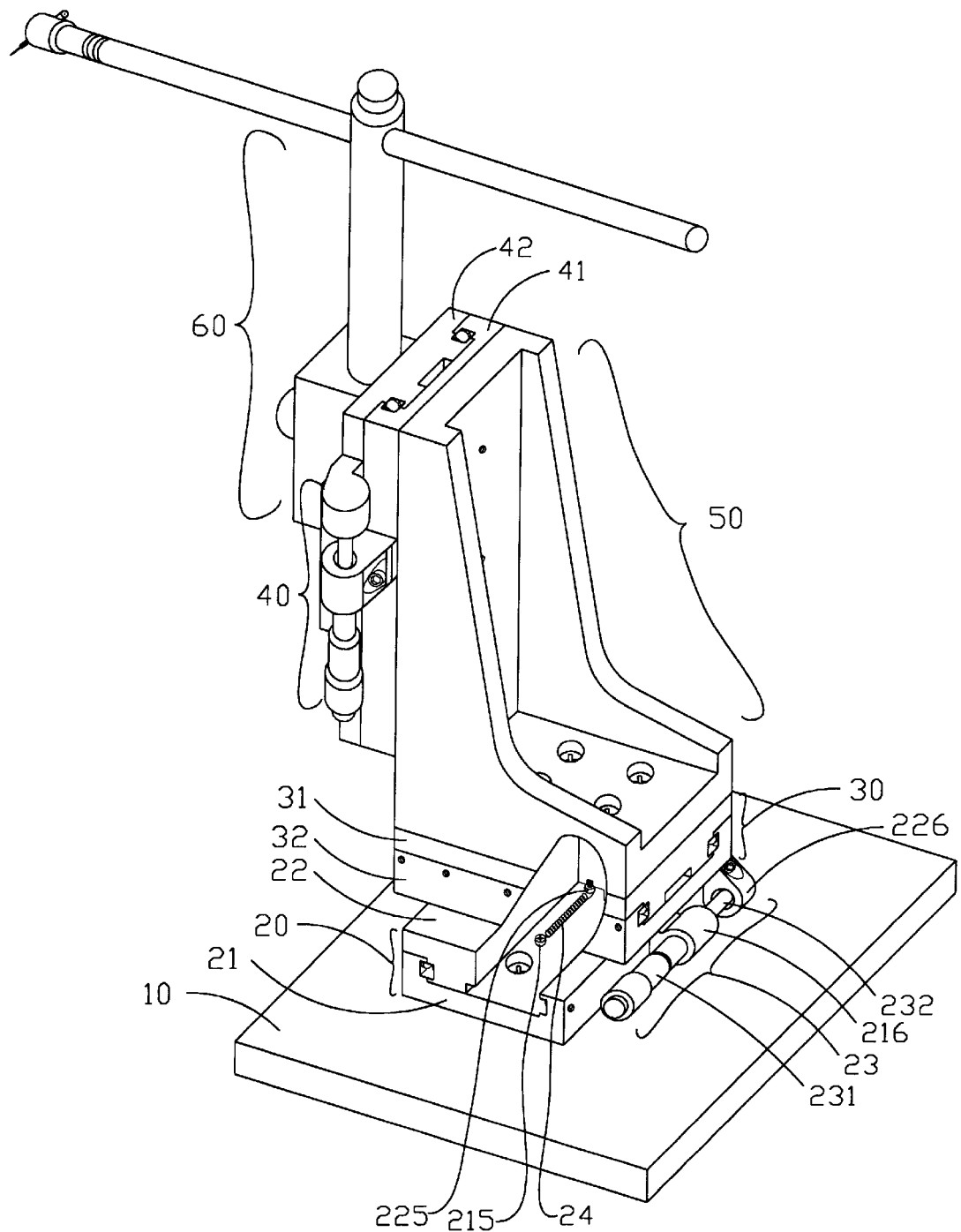
FIG. 3C shows the view of the shifting assemblage containing spring.

Referring to FIG. 3, an X-direction shifting assemblage 20, located on the base 10, includes a plate 21, a movable stage 22, and a micrometer 23. The plate 21, fixed on the base, approximates an U-shape structure in which two X-direction extended side walls and a bottom exist. Each of the side walls contains an X-direction extended trench 213. FIG. 3B shows the front view of the X-direction shifting assemblage 20. Two cylindrical tracks 214 are fixed in each trench. On the bottom of the plate, a lower spring-fixing screw 215 fixes an end of a spring 24 (see FIG. 3C simultaneously). The movable stage 22, located on the plate 21, approximates a T-shape structure. Further, the convex part is located in the concave of the plate and contains a trench 222 on each side wall of it. Also, two cylindrical tracks 223 are fixed in each trench 222. The trench 222 and tracks 223 are face to face with the trench 213 and the tracks 214 respectively; therein, some steel balls 25, settled among and keep contacting with the four tracks, arrange along X-direction axis (see FIG. 3A simultaneously). By the steel balls 25, the movable stage can move continuously along the X-direction axis. Bottom of the convex of the movable stage 22 contains a trench 224 extending in X-direction. In the trench 224, an upper spring-fixing screw 225 fixes the other end of the spring 24 described above. Moreover, when the movable stage 22 is moved away the original position, the spring 24 will generate a force in the opposite direction. The micrometer 23, located against the plate 21, is fixed on the side wall of the plate 21 by a micrometer hold 216. The micrometer 23 includes a scale wheel 231 and a metal rod 232, The metal rod 232 is located at the front of the scale wheel 231 and contacts with the protuberance 226 which is on the side wall of the movable stage 22. It can be shifted in X-direction by turning the scale wheel 231 and then controls the movement of the movable stage 22 along X-direction axis. In detail, the movable stage 22 is pushed out as the rod 232 lengthens, and pulled back by spring 24 as the rod 232 shortens. The scale wheel contains the scales from 0 to 50. The movable stage will be moved about 0.01 mm when one more scale is got.

Referring back to FIG. 2, an Y-direction shifting assemblage 30, located on the X-direction shifting assemblage 20, has the very same structure as X-direction one 20. Its plate 31 is fixed on the movable stage 22 of the X-direction shifting assemblage 20 and controls the movement of the movable stage 32 in Y-direction.

A L-shape support 50, fixed on the movable stage 32 of Y-direction shifting assemblage 30, is used to support the Z-direction shifting assemblage 40 and extracting assemblage 60.

A Z-direction shifting assemblage 40, located against the L-shape support, has the very same structure as X-direction one 20 and Y-direction one 30. Its plate 41 is fixed on the side wall of the L-shape support and controls the movement of the movable stage 42 in Z-direction.

Figure 4:
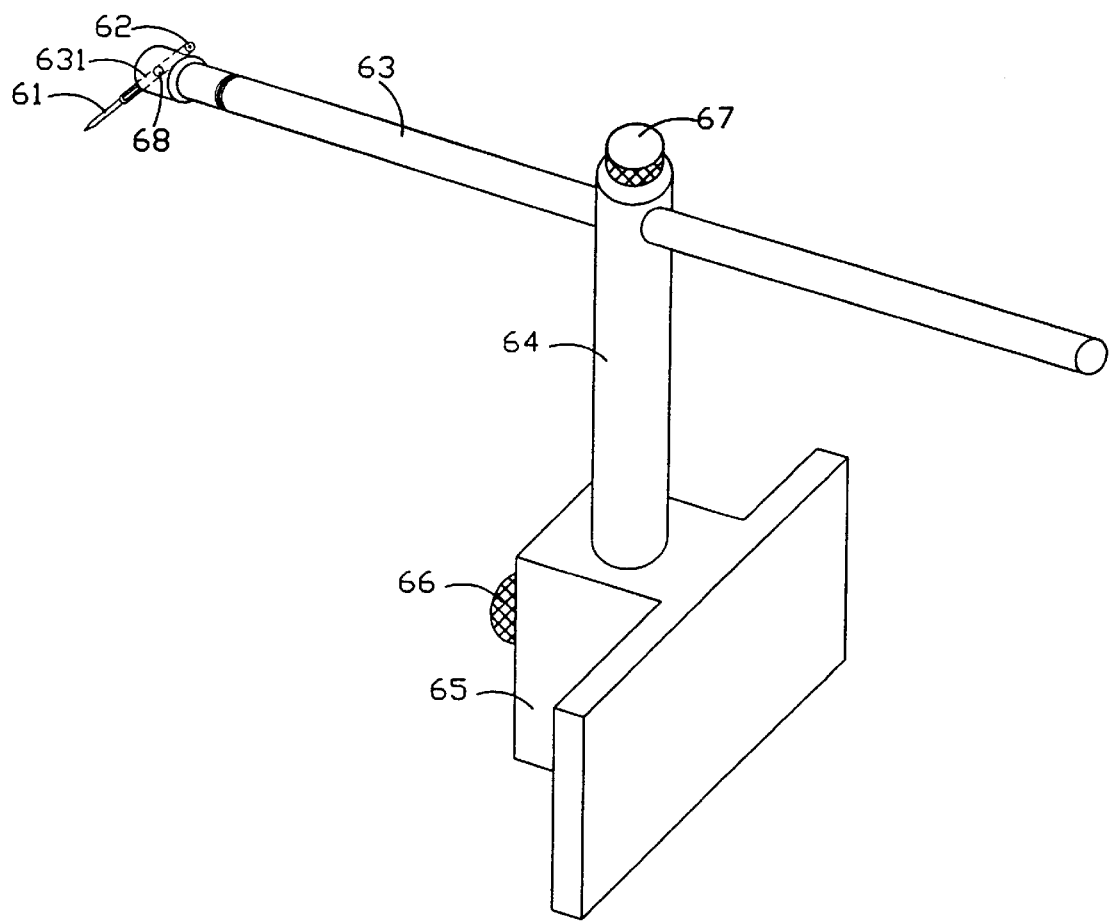
FIG. 4 shows the whole view of the extracting assemblage.

Referring to FIG. 4, an extracting assemblage, located against Z-direction shifting assemblage, comprises: a stand hold 65 fixed on the movable stage 42 of the Z-direction shifting assemblage 40, a stand 64 locked in the stand hold 65, an arm 63 locked in a hole through top part of the stand 64, a contractible fastener 62 locked in a sloping hole through the arm 63, and a glass pipette 61 fastened by the contractible fastener 62, and three locking screws 66, 67, 68.

Figure 4A:
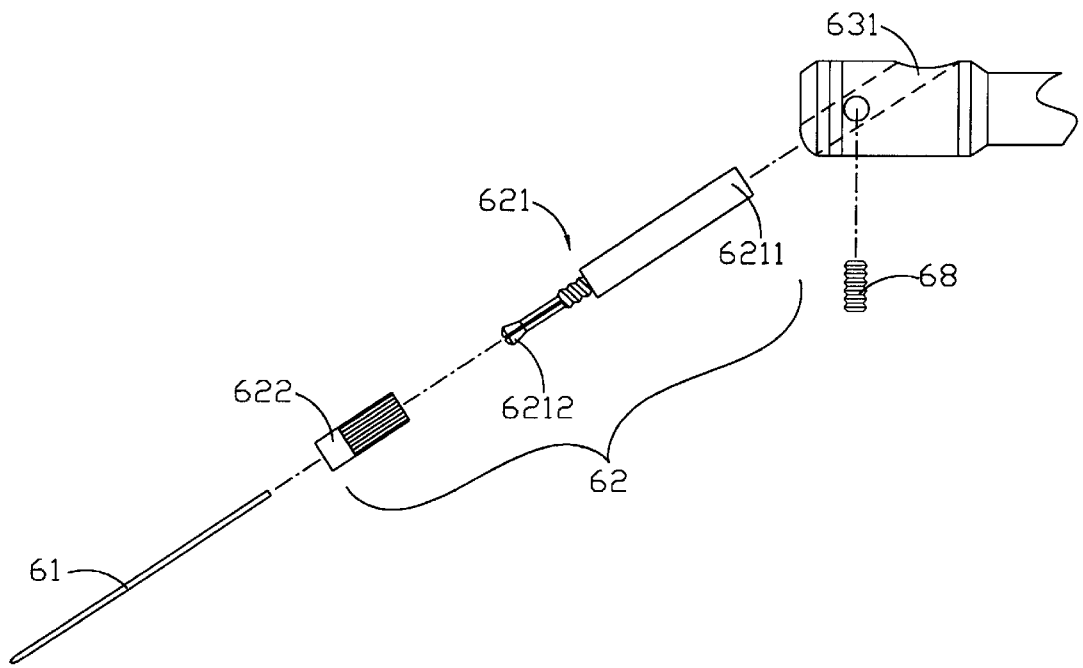
FIG. 4A shows the cut-off view of the extracting fastener.
Figure 4B:
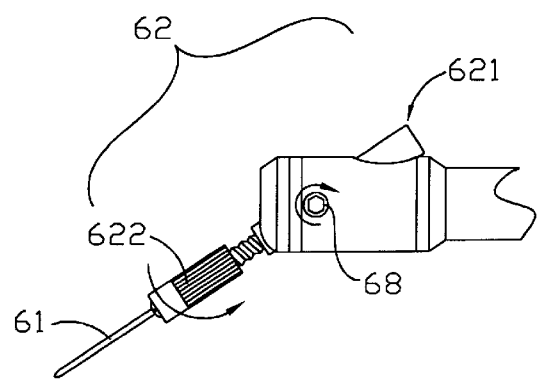
FIGS. 4B–4C show the views of the combination of both the glass pipette and the extracting fastener.
Figure 4C:
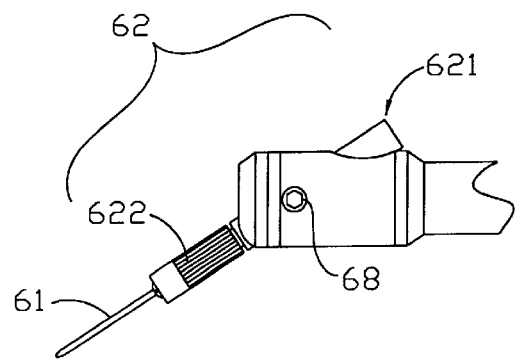

Referring to FIGS. 4A, 4B, and 4C, a fastener hole 631 exists through an end part of the arm 63 and is at a 30 degrees angle with the arm's main axis. Beside the fastener hole 631, the fastener-locking screw 68 used to lock the contractible fastener 62 exists. The contractible fastener 62 comprises a body 621 and a lock nut 622. The body 621 includes a cylinder part 6211 on which a screw thread exists, and three contractible pieces 6212 which are made of metal and arranged in a circle. The beginning of each piece 6212 connects to the cylinder part 6211 and the end has a bulge positioned outside of the circle. The lock nut 622 matches the screw thread on the cylinder part 6211 and contracts the three contractible pieces 6212 to fasten the glass pipette 61. The glass pipette 61 is the device used to contact with the specimen directly. It's about 5 cm long, the diameter of its end side is 1 mm, and the diameter of its beginning side is less than 2 μm. The end side is fastened in the contractible fastener 62 and the beginning side is used to contact with the specimen.

Figure 5:
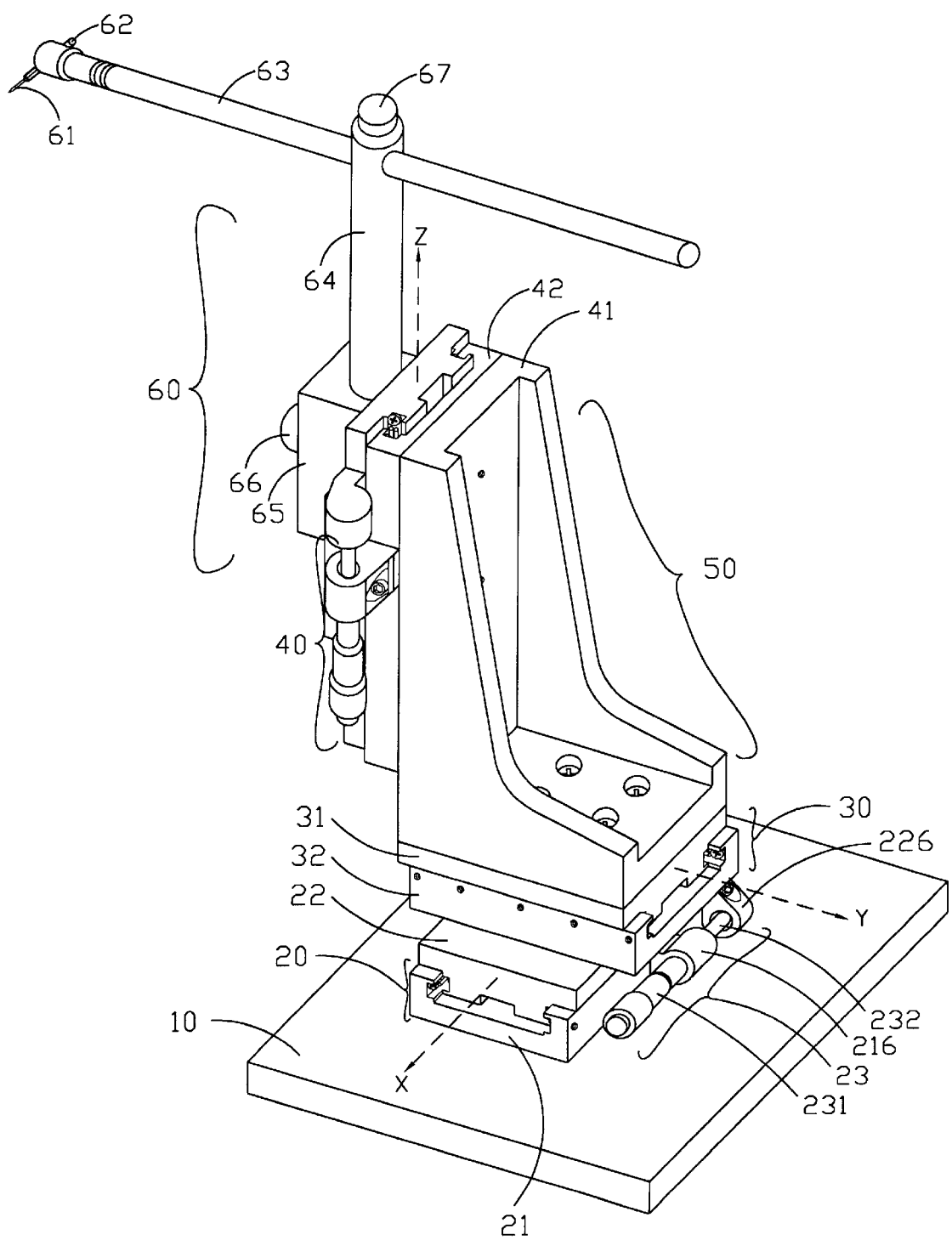
FIG. 5 shows the view of the moving shifting assemblages.

The present invention is named '3-direction TEM specimen extractor'. For the extracting, charges are firstly loaded onto the surface of the glass pipette, then the specimen can be extracted by the electrostatic attraction. The contractible fastener 62 is used to fasten the glass pipette 61. It's easy to manipulate and fast to change the pipette. The movements of the glass pipette is controlled by X, Y, and Z-direction shifting assemblages 20, 30, 40. In addition, the ball-track devices provide the glass pipette 61 with continuous movements in X, Y, and Z directions. Then, the three micrometers control its moving distances in X, Y, and Z directions. The view of the moving shifting assemblages is shown in FIG. 5.

Although specific embodiments have been illustrated and described, it will be obvious to those skilled in the art that various modifications may be made without departing from what is intended to be limited solely by the appended claims.

What is claimed is:

1. An apparatus for extracting a specimen of transmission electron microscope (TEM) comprising:

a base;

a first shifting assemblage, located on said base, including a first plate, a first movable stage, and a first micrometer, wherein said first plate is fixed on said base, said first movable stage located on said first plate comprises a first protuberance, and said first micrometer is locked on side wall of said first plate;

a second shifting assemblage, located on said first shifting assemblage, including a second plate, a second movable stage, and a second micrometer, wherein said second plate is fixed on said first movable stage, said second movable stage located on said second plate comprises a second protuberance, and said second micrometer is locked on side wall of said second plate;

a L-shape support, fixed on said second shifting assemblage;

third shifting assemblage, located on the side wall of said L-shape support, including a third plate, a third movable stage, and a third micrometer, wherein said third plate is fixed on the side wall of said L-shape support, said third movable stage located on said third plate comprises a third protuberance, and said third micrometer is locked on side wall of said third plate; and an extracting assemblage, located on said third shifting assemblage, including a stand hold fixed on said third movable stage, a stand locked in said stand hold, an arm locked in a hole through said stand, a fastener locked in a sloping hole through the arm, and a pipette fastened by said fastener.

2. The apparatus according to claim 1, wherein said first micrometer comprises:

a first rod, the front side of which contacts with said first protuberance, located at the fore part of said first micrometer and used to control the movement of said first movable stage along X-direction axis;

a first scale wheel, located behind said first rod and used to control the movement of said first rod along X-direction axis.

3. The apparatus according to claim 1, wherein said first shifting assemblage further comprises a first spring, one end of which is locked on top surface of said first plate and the other end is locked on bottom surface of said first movable stage.

4. The apparatus according to claim 1, wherein said first shifting assemblage further comprises a first ball-track device, used to provide said first plate with continuous movement, including:
  four X-direction tracks, of which two are fixed to said first plate and the other two to said first movable stage, paralleled each other; and
  at least one steel ball which is settled among and contacts with said four X-direction tracks.

5. The apparatus according to claim 1, wherein said second micrometer comprises:
  a second rod, the front side of which contacts with said second protuberance, located at the fore part of said second micrometer and used to control the movement of said second movable stage along Y-direction axis;
  a second scale wheel, located behind said second rod and used to control the movement of said second rod along Y-direction axis.

6. The apparatus according to claim 1, wherein said second shifting assemblage further comprises a second spring, one end of which is locked on top surface of said second plate and the other end is locked on bottom surface of said second movable stage.

7. The apparatus according to claim 1, wherein said second shifting assemblage further comprises a second ball-track device, used to provide said second plate with continuous movement, including:
  four Y-direction tracks, of which two are fixed to said second plate and the other two to said second movable stage, paralleled each other; and
  at least one steel ball which is settled among and contacts with said four Y-direction tracks.

8. The apparatus according to claim 1, wherein said third micrometer comprises:
  a third rod, the front side of which contacts with said third protuberance, located at the fore part of said third micrometer and used to control the movement of said third movable stage along Z-direction axis;
  a third scale wheel, located behind said third rod and used to control the movement of said third rod along Z-direction axis.

9. The apparatus according to claim 1, wherein said third shifting assemblage further comprises a third spring, an end of which is locked on top surface of said third plate and the other end is locked on bottom surface of said third movable stage.

10. The apparatus according to claim 1, wherein said third shifting assemblage further comprises a third ball-track device, used to provide said third plate with continuous movement, including:
  four Z-direction tracks, of which two are fixed to said third plate and the other two to said third movable stage, paralleled each other; and
  at least one steel ball which is settled among and contacts with said four Z-direction tracks.

11. The apparatus according to claim 1, wherein said fastener comprises a contractible fastener.

12. The apparatus according to claim 11, wherein said contractible fastener comprises:
  a body, including:
    a cylinder part on which a screw thread exists,
    three contractible pieces which arrange in a circle, the beginning of each connects to said cylinder part and the end has a bulge on outside surface; and
  a lock nut, which matches the screw thread on said cylinder part and contracts said three contractible pieces to fasten said pipette.

13. The apparatus according to claim 1, wherein said pipette comprises a tiny glass pipette with a sharp end used to contact to said specimen.

14. The apparatus according to claim 1, wherein the said specimen is extracted by firstly loading charges on a surface of said pipette, and subsequently extracting said specimen with the electrostatic attraction.

15. A apparatus for extracting a TEM specimen comprises:
  an extracting assemblage comprises a pipette; and
  a shifting assemblage, connecting to said extracting assemblage, used to control the movement of said pipette.

16. The apparatus according to claim 15, wherein said shifting assemblage comprises a micrometer used to control the distance of the movement of said pipette.

17. The apparatus according to claim 15, wherein said shifting assemblage further comprises a ball-track device used to result in continuous movement of said pipette.

18. The apparatus according to claim 15, wherein said shifting assemblage comprises a fastener used to fasten said pipette.

19. The apparatus according to claim 15, wherein said pipette comprises tiny glass pipette.

* * * * *